United States Patent [19]

Koehler

[11] Patent Number: 4,796,608

[45] Date of Patent: Jan. 10, 1989

[54] SHOCK WAVE GENERATOR FOR AN APPARATUS FOR NON-CONTACTING DISINTEGRATION OF CALCULI IN THE BODY OF A LIFE FORM

[75] Inventor: Georg Koehler, Geisfeld, Fed. Rep. of Germany

[73] Assignee: Siemens Aktiengesellschaft, Berlin and Munich, Fed. Rep. of Germany

[21] Appl. No.: 49,518

[22] Filed: May 14, 1987

[30] Foreign Application Priority Data

Jun. 16, 1986 [DE] Fed. Rep. of Germany ....... 3620189

[51] Int. Cl.[4] ............................................. A61B 17/22

[52] U.S. Cl. .................................. 128/24 A; 128/328

[58] Field of Search ............. 128/328, 24 A; 367/175, 367/142; 181/142, 118

[56] References Cited

U.S. PATENT DOCUMENTS 2,648,837 8/1953 Mounce ............................... 340/400

4,669,472 6/1987 Eisenmenger ....................... 128/328

4,674,505 6/1987 Pauli et al. .......................... 128/328

*Primary Examiner*—Ruth Smith

*Attorney, Agent, or Firm*—Hill, Van Santen, Steadman & Simpson

[57] ABSTRACT

A shock wave generator for use in an apparatus for non-contacting disintegration of calculi in the body of a life form (extracorporeal lithotripter) having a coil with helical windings and a membrane of electrically conductive material disposed opposite the coil, the membrane terminating a space filled with a liquid. The coil is connectable to a high voltage supply. The coil has two layers connected in series and overlapping each other in parallel planes, with the respective current direction and winding direction of the layers being selected in combination to intensify the magnetic fields of each layer. A layer of the coil having a smaller voltage difference relative to the membrane is disposed immediately adjacent the membrane. The arrangement increases the useful life of the membrane without significantly reducing the efficiency of converting the electrical energy into shock wave energy.

12 Claims, 2 Drawing Sheets

SHOCK WAVE GENERATOR FOR AN APPARATUS FOR NON-CONTACTING DISINTEGRATION OF CALCULI IN THE BODY OF A LIFE FORM

BACKGROUND OF THE INVENTION

1. Field of the Invention

The present invention is directed to a shock wave generator for use in an extracorporeal lithotripter, and in particular to such a shock wave generator having a membrane formed of electrically conductive material disposed opposite the coil and terminating a volume filled with fluid.

2. Description of the Prior Art

German OS No. 33 12 014 discloses a shock wave generator having a membrane disposed parallel to the coil. The shock waves are generated by connecting the coil to a high voltage supply, containing a capacitor charged to several kilovolts, for example, 20 kV. The energy stored in the capacitor discharges rapidly into the coil, causing the coil to rapidly generate a magnetic field. At the same time, a current is induced in the membrane, this current having an opposite plurality to the current flowing in the coil, and consequently generating an opposing magnetic field, which causes the membrane to rapidly move away from the coil. The shock wave thereby generated in the adjacent volume filled with liquid, for example water, is focussed with known means to the calculi, for example kidney stones, disposed within the body of a life form, and causes disintegration thereof.

In order to achieve the highest possible conversion of the electrical energy output of the high voltage supply into shock energy, it is necessary in such known shock wave generators to attach the membrane as close as possible to the coil. Due to the difference in potential necessarily existing between the coil and the membrane, however, this is only possible within certain limits because a minimum spacing must be observed in order to avoid arcing between the membrane and the coil. Arcing deteriorates the effectiveness of the shock wave generator, and also leads to damage of the membrane, the latter lessening the useful life thereof. In conventional shock wave generators, therefore, the spacing between the membrane and the coil must be selected so as to maintain an adequate useful life of the membrane, thereby necessarily resulting in an unsatisfactory efficiency in the conversion of electrical energy into shock energy.

SUMMARY OF THE INVENTION

It is an object of the present invention to provide a shock wave generator having a coil and a membrane wherein the membrane exibits a high useful life without substantial reduction in the efficiency of the energy conversion.

In accordance with the principles of the present invention, the above object is achieved in a shock wave generator having a coil consisting of two layers or piles connected in series and overlying each other in parallel planes. The current direction and winding direction of the two layers are matched to each other so as to intensify the total magnetic field resulting from the magnetic field generated by each layer. The layer of the coil having the smaller voltage difference relative to the membrane is disposed immediately adjacent the membrane. The invention makes use of the fact that the high voltage decreases over the length of the coil. In a two layer coil, therefore, a maximum voltage difference will be present between at least one layer of the coil and the membrane, this maximum voltage difference being lower than the maximum voltage difference which is present between the membrane and a single layer coil given the same magnitude of the high voltage.

Arcing between the membrane and the coil can consequently be avoided despite a small distance between the membrane and the coil by arranging the coil layer having a smaller voltage difference relative to the membrane directly adjacent the membrane. Because the two layers of the coil are connected in series and are congruently arranged in parallel planes, with the current and winding directions of the two layers being adapted to each other in the sense of intensifying the overall magnetic field, the coil also generates a stronger magnetic field than a single layer coil given the same magnitude of high voltage and the same coil diameter. This is caused by higher eddy currents being induced in the membrane and a stronger opposing magnetic field thereby being generated. The overall combination has the final result in generating stronger shock waves in the volume filled with liquid. Arcing between the coil and the membrane are effectively avoided, resulting in an increase life of the membrane without sacrificing the efficiency of the energy conversion of electrical energy into shock energy.

High shock wave pressures can be achieved with the shock wave generator disclosed herein compared to conventional generators utilizing the same magnitude of high voltage, or alternatively the same shock wave pressure can be achieved as in known devices but using a lower high voltage than in those conventional devices. If a lower high voltage value is used, a further reduction in the distance between the membrane and the layer of the coil adjacent thereto is possible.

Regardless of whether the same or a lower high voltage is used in the generator disclosed herein, in comparison to conventional generators, the conversion of electrical energy into shock energy will be improved because the shock wave generated by the generator disclosed herein will have shorter rise times. This is because the capacitor in the high voltage supply can be charged to a higher charging voltage in comparison to that of a shock wave generator having a single layer coil. The capacitor can either generate a greater energy output (which increases with the square of the charging voltage) or, given the same input energy available, its capacitance can be reduced. Reducing the capacitance results in a higher natural frequency of the resonant circuit formed by the coil and the capacitor, resulting in a shorter rise time of the current flowing through the coil, and thus a shorter rise time of the shock wave. This is a significant advantage for use in disintegrating calculi.

In one embodiment of the invention, the two layers of the coil are wound in opposite directions, with their respectively innermost windings connected to each other and their respectively outermost windings connected to the high voltage supply. This permits the coil to be manufactured in a simple manner, and results in a low coil thickness because a special connection between the two layers of the coil, which would otherwise be required, can be omitted. It is preferable from a manufacturing standpoint if both layers of the coil have the same number of turns. In a preferred embodiment, the outermost winding of the layer of the coil immediately adjacent to the membrane is at the same potential as the membrane. The membrane may be at ground potential, thus assuring that no high voltage is adjacent to the liquid disposed in the volume, which is a significant safety measure because this liquid may potentially come into contact with the life form or with operating personnel.

DESCRIPTION OF THE PREFERRED EMBODIMENTS

Figure 1:
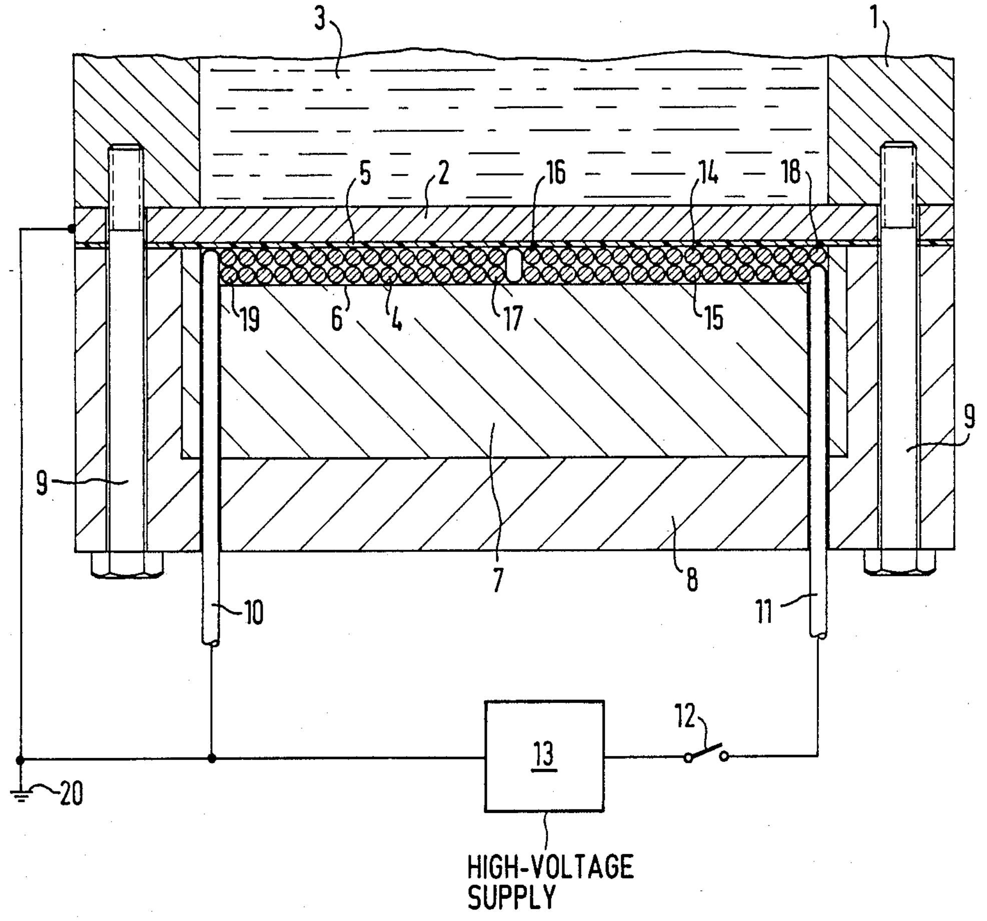
FIG. 1 shows a side sectional view of a portion of a shock wave generator constructed in accordance with the principles of the present invention, showing only those components necessary to describe the invention.

A shock wave generator constructed in accordance with the principles of the present invention is shown in FIG. 1 and has a housing 1 containing a volume 3 filled with a liquid and terminated by a membrane 2 consisting of electrically conductive material. A coil 4 having helical turns is disposed opposite the membrane 2, and an insulating foil 5 is disposed between the membrane 2 and the coil 4. The windings of the coil 4 are arranged on a seating surface 6 of an insulator 7 which is received in a cap or cover 8. The membrane 2, the insulating foil 5 and the cover 8 containing the insulator 7 and the coil 4 are secured to the housing 1 with bolts 9.

For fixing the coil to the seating surface 6 of the insulator 7, the space between the insulating foil 5 and the seating surface 6 is filled with an electrically insulating casting resin, which is not shown in the interest of clarity.

Figure 2:
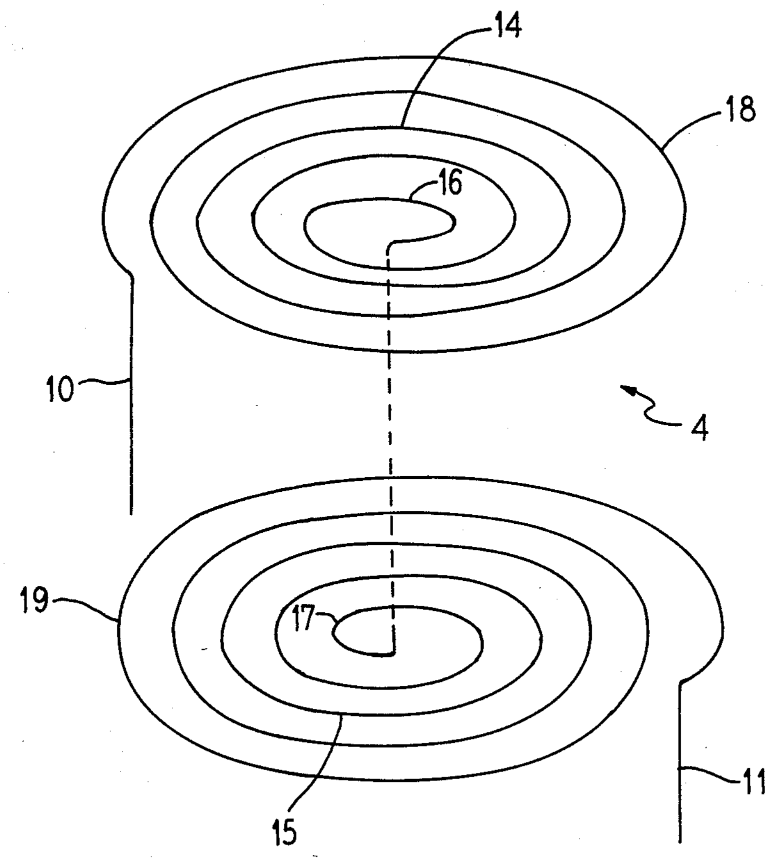
FIG. 2 is a perspective, exploded view schematically showing the connection of the windings of the coil in the shock wave generator of FIG. 1.

Terminals 10 and 11 are provided which extend to the exterior of the unit through bores in the insulator 7 and the cover 8. The coil is connectable via these terminals to a switch 12 and a high voltage supply 13. The high voltage supply 13 provides a current surge or pulse to the coil 4 when the switch 12 is closed, so that the membrane 2 is suddenly repelled from the coil 4, resulting in the formation of a shock wave in the liquid in the volume 3. Voltage differences arise between the membrane 2 and the individual windings of the coil 4 as a result of the high voltage across the coil 4. The coil 4 is therefore comprised of two layers 14 and 15 which are arranged congruently in parallel planes. As schematically shown in FIG. 2, the two layers 14 and 15 of the coil 4 are wound in opposite directions, and are connected in series by connecting their respectively innermost windings 16 and 17, so that the magnetic fields of both layers 14 and 15 of the coil 4 intensify each other when connected to the high voltage supply 13 via their respectively outermost windings 18 and 19. The two layers 14 and 15 of the coil preferably have the same number of turns.

The outermost winding 18 of the layer 14 of the coil disposed immediately adjacent or proximate to the membrane 2 preferable is at the same potential as the membrane 2, and this potential is preferably ground potential, as indicated at 20. There is consequently a lower voltage difference between the layer 14 of the coil 4 immediately adjacent to the membrane 2, than between the membrane 2 and the layer 15 of the coil 4 remote from the membrane.

A shock wave generator is shown in the above exemplary embodiment having a planar membrane 2; however, it is also possible to construct shock wave generators having a differently shaped membrane, for example, a spherically shaped membrane without departing from the invention principles disclosed herein.

Although modifications and changes may be suggested by those skilled in the art it is the intention of the inventor to embody within the patent warranted hereon all changes and modifications as reasonably and properly come within the scope of his contribution to the art.

I claim as my invention:

1. A shock wave generator comprising:
   a housing having a volume containing a shock wave transmitting medium;
   a membrane consisting of electrically conductive material, said membrane terminating said volume on one side;
   means for applying a first potential to said membrane;
   a high voltage source having terminal means for supplying a second potential and terminal means for supplying a third potential, said high voltage source being capable of generating a current pulse;
   a coil having two terminals, said coil being disposed next to said membrane and having two layers of helical windings disposed congruently in respective parallel planes, said layers being connected in series and being wound in respective winding directions such that the respective magnetic fields of said two layers intensify each other upon a current flowing through said coil; and
   means for respectively connecting said terminals of said coil to said terminal means for supplying said second and third potentials of said high voltage source for respectively applying said second and third potentials to said terminals of said coil and for releasing said current pulse into said coil, the high voltage dropping along said coil, thereby generating respective voltage differences in said layers of said coil relative to said membrane and one of said layers exhibiting a smaller voltage difference relative to said membrane than the other of said layers, when said coil is connected to said high voltage source, and said one layer exhibiting said smaller voltage difference being disposed immediately adjacent said membrane.

2. A shock wave generator as claimed in claim 1, wherein said layers of said coil are wound in opposite winding directions, and wherein each of said layers has an innermost winding, said innermost windings being connected to each other, and wherein each layer has an outermost winding, said outermost windings being respectively connected by said means for connecting to said terminal means for supplying said second and third potentials of said high voltage source.

3. A shock wave generator as claimed in claim 1, wherein said one layer of said coil disposed adjacent said membrane has an outermost winding which is connected by said means for connecting to said means for supplying said second potential, said second potential being equal to said first potential applied to said membrane.

4. A shock wave generator as claimed in claim 1, wherein said first and second potentials are ground potential.

5. A shock wave generator as claimed in claim 1, wherein each of said layers has the same number of windings.

6. A shock wave generator as claimed in claim 1, wherein said membrane is planar.

7. A shock wave generator comprising:

a housing having a volume containing a shock wave transmitting medium;

a membrane consisting of electrically conductive material, said membrane terminating said volume on one side;

means for applying a first potential to said membrane;

a high voltage source having terminal means for supplying a second potential and terminal means for supplying a third potential, said high voltage source being capable of generating a current pulse;

a coil having two terminals, said coil being disposed in proximity to said membrane and having two layers of helical windings disposed congruently in respective parallel planes, said layers being connected in series and being wound in respective winding directions such that the respective magnetic fields of said two layers intensify each other upon a current flowing through said coil; and means for respectively connecting said terminals of said coil to said terminal means for supplying said second and third potentials of said high voltage source for respectively applying said second and third potentials to said terminals of said coil and for releasing said current pulse into said coil, the high voltage dropping along said coil, thereby generating respective voltage differences in said layers of said coil relative to said membrane and one of said layers exhibiting a smaller voltage difference relative to said membrane than the other of said layers, when said coil is connected to said high voltage source, and said one layer exhibiting said smaller voltage difference being disposed closer to said membrane than the other of said layers.

8. A shock wave generator as claimed in claim 7, wherein said one layer of said coil disposed closer to said membrane has an outermost winding which is connected by said means for connecting to said means for supplying said second potential, said second potential being equal to said first potential applied to said membrane.

9. A shock wave generator as claimed in claim 7, wherein said first and second potentials are ground potential.

10. A shock wave generator as claimed in claim 7, wherein said layers of said coil are wound in opposite winding directions, and wherein each of said layers has an innermost winding, said innermost windings being connected to each other, and wherein each layer has an outermost winding, said outermost windings being respectively connected by said means for connecting to said terminal means for supplying said second and third potentials of said high voltage source.

11. A shock wave generator as claimed in claim 7, wherein each of said layers has the same number of windings.

12. A shock wave generator as claimed in claim 7, wherein said membrane is planar.

* * * * *